United States Patent
Dassonville et al.

(10) Patent No.: US 10,485,601 B2
(45) Date of Patent: Nov. 26, 2019

(54) SURGICAL INSTRUMENTATION AND METHODS FOR IMPLANTING AN ELONGATED IMPLANT IN A LONG BONE

(71) Applicant: Tornier, Montbonnot-Saint-Martin (FR)

(72) Inventors: Benjamin Dassonville, Saint Hilaire du Touvet (FR); Pierric Deransart, Saint Martin d'Uriage (FR); Jean-Emmanuel Cardon, Domene (FR); Gilles Walch, Lyons (FR); Pascal Boileau, Nice (FR)

(73) Assignee: TORNIER, Montbonnot-Saint-Martin (FR)

( * ) Notice: Subject to any disclaimer, the term of this patent is extended or adjusted under 35 U.S.C. 154(b) by 155 days.

(21) Appl. No.: 15/369,178

(22) Filed: Dec. 5, 2016

(65) Prior Publication Data
US 2017/0164992 A1 Jun. 15, 2017

(30) Foreign Application Priority Data
Dec. 11, 2015 (FR) ...................................... 15 62237

(51) Int. Cl.
*A61B 17/17* (2006.01)
*A61B 17/92* (2006.01)
(Continued)

(52) U.S. Cl.
CPC ........ *A61B 17/921* (2013.01); *A61B 17/1725* (2013.01); *A61B 17/72* (2013.01);
(Continued)

(58) Field of Classification Search
CPC .............. A61B 17/1725; A61B 17/921; A61B 2017/90
See application file for complete search history.

(56) References Cited

U.S. PATENT DOCUMENTS 6,039,739 A 3/2000 Simon
2009/0157077 A1* 6/2009 Larsen ............... A61B 17/1725
606/62

FOREIGN PATENT DOCUMENTS

CA 2 646 726 9/2007
EP 1 759 643 3/2007
(Continued)

OTHER PUBLICATIONS

Search Report issued in French Application No. 1562237, dated Apr. 26, 2016, in 2 pages.

*Primary Examiner* — Julianna N Harvey
(74) *Attorney, Agent, or Firm* — Knobbe, Martens, Olson & Bear, LLP

(57) ABSTRACT

The instrumentation makes it possible to implant in a long bone, such as the humerus, the femur or the tibia, an implant, such as an osteosynthesis nail or a prosthetic rod, defining a longitudinal axis and including, in alignment along the longitudinal axis, two opposite terminal parts and a running part that separates the two terminal parts from one another. The instrumentation comprises a targeting ancillary tool that is adapted to target one and/or the other of the terminal parts of the implant, if applicable percutaneously, along at least one targeting axis that is transverse, or even perpendicular, to the longitudinal axis. The targeting ancillary tool is designed to be fastened laterally to the running part of the implant so as to position the targeting ancillary tool and the implant relative to one another in a predetermined configuration.

28 Claims, 15 Drawing Sheets

(51) Int. Cl.
*A61B 17/72* (2006.01)
*A61B 17/74* (2006.01)
*A61B 17/88* (2006.01)
*A61B 17/90* (2006.01)

(52) U.S. Cl.
CPC .......... *A61B 17/74* (2013.01); *A61B 17/8872* (2013.01); *A61B 2017/90* (2013.01); *A61B 2017/922* (2013.01)

(56) References Cited

FOREIGN PATENT DOCUMENTS

| EP | 2 548 523 | 1/2013 |
|---|---|---|
| EP | 3 178 418 | 6/2017 |

* cited by examiner

SURGICAL INSTRUMENTATION AND METHODS FOR IMPLANTING AN ELONGATED IMPLANT IN A LONG BONE

The present invention relates to a surgical instrumentation for implanting an elongated implant, such as an osteosynthesis nail or a prosthetic rod, in a long bone, such as the humerus, the femur or the tibia. It also relates to a surgical assembly including an elongated implant and such an instrumentation. It also relates to associated surgical methods.

After the fracture of a long bone, for example the humerus, an osteosynthesis nail is frequently used, placed in an extended manner along its length in the medullary cavity of the diaphysis of the bone. A terminal part of the nail is provided to emerge from this medullary cavity, at the head of the bone, while the rest of the nail, which extends in longitudinal axial alignment with the emerging part, is arranged inside the medullary cavity. This nail makes it possible to stabilize the bone fragments initially separated by the fracture to be treated.

To limit the incision in the flesh and other soft parts around the bone fracture site as much as possible, the nail is frequently inserted into the bone by slipping it therein along its longitudinal axis through an end of the medullary cavity, which has previously been opened only in the extension of the medullary cavity. A targeting ancillary tool is next used that has guiding through holes to place, at several heights of the nail, transverse fastening screws between the nail and the bone. Each of these fastening screws is engaged, percutaneously and along a targeting axis that is transverse to the longitudinal direction of the nail, inside a complementary passage defined through the nail: the appropriate relative positioning between the guide hole and the aforementioned passage is provided by the fact that the targeting ancillary tool and the nail are fixedly connected to one another in a predetermined configuration. In practice, the fixed connection between the targeting ancillary tool and the nail is provided by a screw, or, more generally, by a mechanical assembly element, which both extends from a bent region of the ancillary tool, arranged across the extension of the nail along the longitudinal direction of the latter, and is designed to engage the corresponding longitudinal end of the nail. One example of such instrumentation is provided by EP 2,548,523. Another example is provided by EP 1,752,643.

The assembly element, such as the aforementioned screw, that provides the fixed connection between the targeting ancillary tool and the nail in a predetermined configuration has the advantage of being minimally invasive with respect to the soft tissues covering the head of the fractured long bone. Furthermore, when the head of this bone has already been considerably destroyed due to the fracture to be treated, the use of this assembly element does not lead to significant further alteration of this head. However, when the fracture to be treated is not the source of substantial fragmentation of the head of the bone, it is understood the use of this assembly element requires piercing the head all the way through in the longitudinal extension of the medullary cavity of the diaphysis of the bone, so that the nail, held at its end by this assembly element, can be inserted inside the medullary cavity through the head. Furthermore, once the nail is in its implantation position, the assembly element is frequently found through the head of the bone, occupying the region of the latter that has been pierced beforehand. It is therefore understood that, for certain types of fracture, using the existing targeting ancillary tools leads to altering the non-fragmented bone parts, and consequently, the cartilage associated therewith, which may be debatable from a surgical perspective.

The aim of the present invention is to propose new instrumentation and new methods for implanting a long implant that, for certain types of long bone fractures, proves less traumatic for the non-fragmented bone parts, or even makes it possible to preserve the latter.

To that end, the invention relates to a surgical instrumentation for implanting an elongated implant, such as an osteosynthesis nail or a prosthetic rod, in a long bone, such as the humerus, the femur or the tibia, the implant defining a longitudinal axis and including, in alignment along the longitudinal axis, two opposite terminal parts and a running part that separates the two terminal parts from one another. This instrumentation comprises a targeting ancillary tool that is adapted to target one and/or the other of the terminal parts of the implant, if applicable percutaneously, along at least one targeting axis that is transverse, or even perpendicular, to the longitudinal axis. This targeting ancillary tool is designed to be fastened laterally to the running part of the implant so as to position the targeting ancillary tool and the implant relative to one another in a predetermined configuration.

The invention also relates to a surgical assembly, including:
  an elongated implant, defining a longitudinal axis and including, in alignment along the longitudinal axis, two opposite terminal parts and a running part that separates the two terminal parts from one another, and
  an instrumentation for implanting the implant in a long bone, such as the humerus, the femur or the tibia, this instrumentation being as defined above.

The invention also relates to a first surgical method for implanting an osteosynthesis nail in a long fractured bone, such as the humerus, the femur or the tibia, said long bone being fractured at least between its proximal end and its diaphysis. The nail has a longitudinal axis and includes, in alignment along the longitudinal axis, two opposite terminal parts and a running part that separates the two terminal parts from one another. In this method, a targeting ancillary tool is fastened laterally to the running part of the nail. During this method, successively:
  a surgical approach is opened by forming an incision in the soft flesh to access the bone, at the fracture thereof between its proximal end and its diaphysis,
  after having separated the proximal end from the diaphysis, a first of the two terminal parts of the nail is inserted, via the approach, into the diaphysis, then the targeting ancillary tool is used to place, percutaneously and along a first targeting axis that is transverse to the longitudinal axis of the nail, at least one first fastening element between the diaphysis and the first terminal part of the nail,
  after having replaced the proximal end in the longitudinal extension of the diaphysis, the targeting ancillary tool is used to place, percutaneously and along a second targeting axis that is transverse to the longitudinal axis of the nail, at least one second fastening element between the proximal end and the second terminal part of the nail,
  the nail is disengaged from the targeting ancillary tool, and
  the approach is closed.

The invention also relates to a second surgical method for implanting a prosthetic rod in a long bone, such as the humerus, the femur or the tibia. The prosthetic rod has a longitudinal axis and includes, in alignment along the longitudinal axis, two opposite terminal parts and a running part that separates the two terminal parts from one another. In this method, a targeting ancillary tool is fastened laterally to the running part of the prosthetic rod. During this method, successively:

a surgical approach is opened by forming an incision in the soft flesh to access the long bone, then the proximal end of the long bone is resected while retaining the diaphysis of the long bone, a first of the two terminal parts of the prosthetic rod is inserted, via the approach, into the diaphysis, then the targeting ancillary tool is used to place, percutaneously and along a targeting axis that is transverse to the longitudinal axis of the prosthetic rod, at least one fastening element between the diaphysis and the first terminal part of the prosthetic rod, the prosthetic rod is disengaged from the targeting ancillary tool, and the approach is closed.

The invention also relates to a third method for implanting a prosthetic rod in a long bone, such as the humerus, the femur or the tibia, said long bone being fractured at least between its proximal end and its diaphysis, said proximal end being fractured in several fragments. The prosthetic rod has a longitudinal axis and includes, in alignment along the longitudinal axis, two opposite terminal parts and a running part that separates the two terminal parts from one another. In this method, a targeting ancillary tool is fastened laterally to the running part of the prosthetic rod. During this method, successively:

a surgical approach is opened by forming an incision in the soft flesh to access the long bone, then at least one of the fragments of the proximal end is removed while retaining the diaphysis of the long bone, a first of the two terminal parts of the prosthetic rod is inserted, via the approach, into the diaphysis, then the targeting ancillary tool is used to place, percutaneously and along a targeting axis that is transverse to the longitudinal axis of the prosthetic rod, at least one fastening element between the diaphysis and the first terminal part of the prosthetic rod, the prosthetic rod is disengaged from the targeting ancillary tool, and the approach is closed.

Whatever the embodiments of the invention, the invention thus goes against the prejudice according to which, to limit the span of the incision in the soft tissue surrounding a fracture of the long bone in which an elongated implant must be implanted, the ancillary tool of the corresponding instrumentation, making it possible to target the implant, can only be fastened to this implant at one of the longitudinal ends thereof, and in a fastening direction projecting in the longitudinal extension of the implant. Indeed, the invention provides for fastening the targeting ancillary tool laterally to a running part of the implant, separating two opposite terminal parts of the implant from one another which, jointly with the running part, are aligned with one another along a longitudinal axis of the implant. This fastening is done using ad hoc fastening means: the ancillary tool is thus designed to be fastened on the lateral side of the running part of the implant, i.e., along a fastening direction that is transverse, or even perpendicular, to the longitudinal axis of the implant, and not in the longitudinal direction of the implant on one of the terminal parts thereof. Of course, using the instrumentation according to the invention leads to forming an incision in the soft tissue along a direction transverse to the long bone undergoing the operation, if applicable over a certain span, because the implant is held laterally by the targeting ancillary tool: the corresponding surgical approach, which may for example be deltopectoral or superolateral, allows the surgeon to view the region of the treated fracture directly, which avoids using perioperative fluoroscopy. In all cases, this operating approach, allowed by the instrumentation according to the invention, preserves non-fragmented bone parts of the long bone, as well as any cartilage associated with these non-fragmented parts. In particular, the head of the bone is preserved, since it no longer needs to be pierced all the way through in the longitudinal extension of the medullary cavity of the diaphysis of the bone in order to insert the implant into the cavity: indeed, this head or the fragments of the latter, separated from the diaphysis due to the fracture to be treated, can simply be moved away from the diaphysis enough not to interfere with the implant during the insertion of the latter into the medullary cavity of the diaphysis.

In practice, the fastening means belonging to the instrumentation according to the invention, which make it possible to fasten the targeting ancillary tool laterally to the implant, can be made with quite varied shapes, which are not limiting with respect to the invention and examples of which are provided below. Thus, in some embodiments, the instrumentation comprises a bar suitable for connecting the targeting ancillary tool and the running part of the implant to one another, extending lengthwise along a fastening axis that is transverse, or even perpendicular, to the longitudinal axis, said bar being provided with a mechanism for lateral connection to the implant, which rigidly connects the bar to the running part of the implant and which guides the relative positioning of the implant and the bar to the predetermined configuration.

Furthermore, the developments of the implant, which make it possible to implant the latter using the instrumentation according to the invention and which therefore cooperate with the aforementioned fastening means, are minimal, or non-essential, as explained in more detail below using examples.

The invention will be better understood upon reading the following description, provided solely as an example and done in reference to the drawings, in which.

Figure 1:
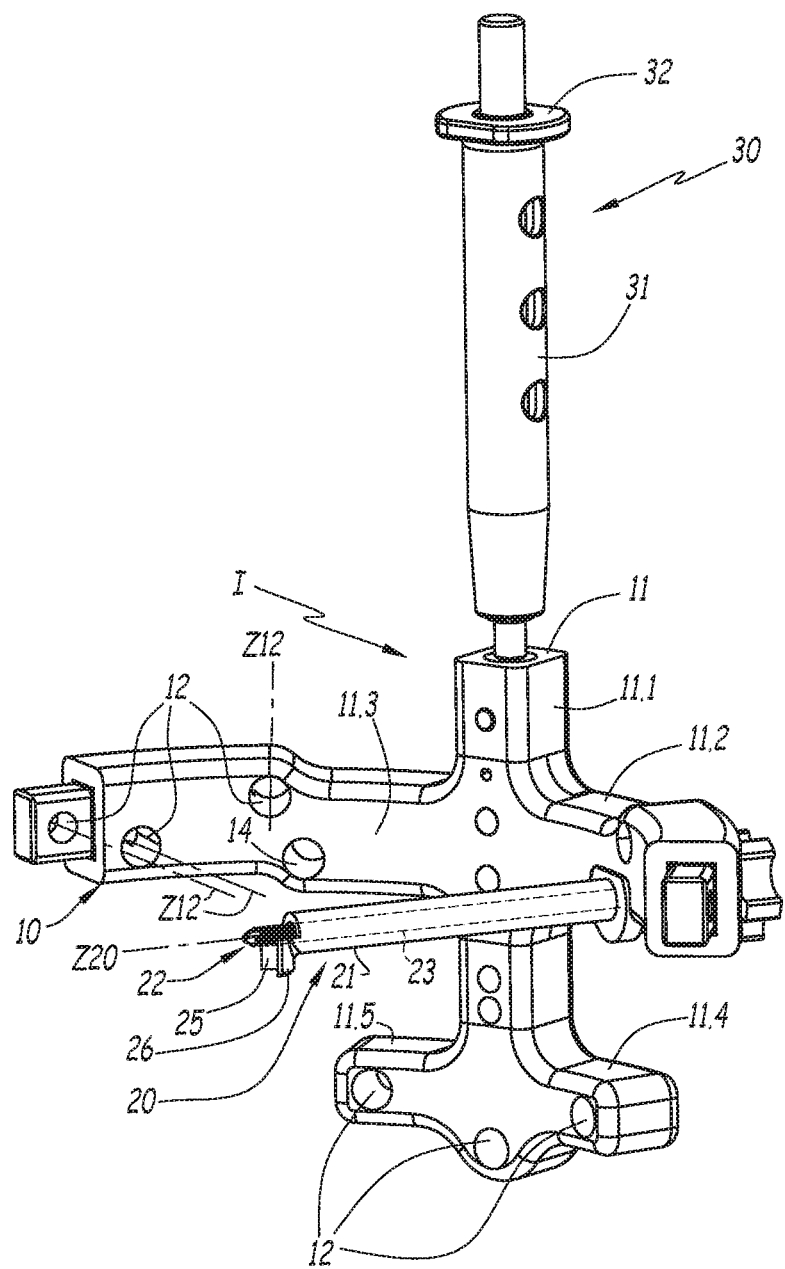
FIG. 1 is a perspective view of a first embodiment of instrumentation according to the invention.
Figure 2:
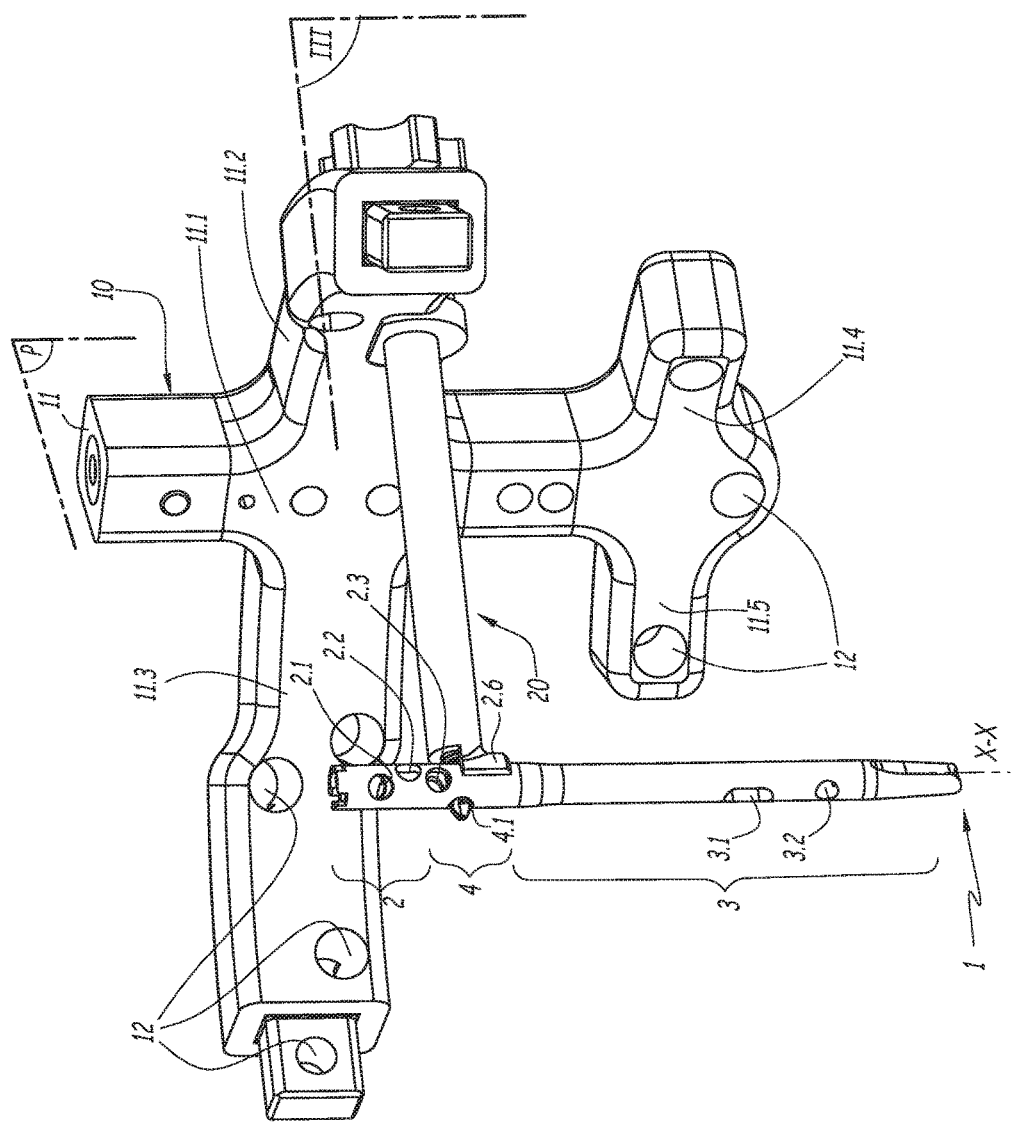
FIG. 2 is a perspective view of the instrumentation of FIG. 1, associated with an osteosynthesis nail.
Figure 3:
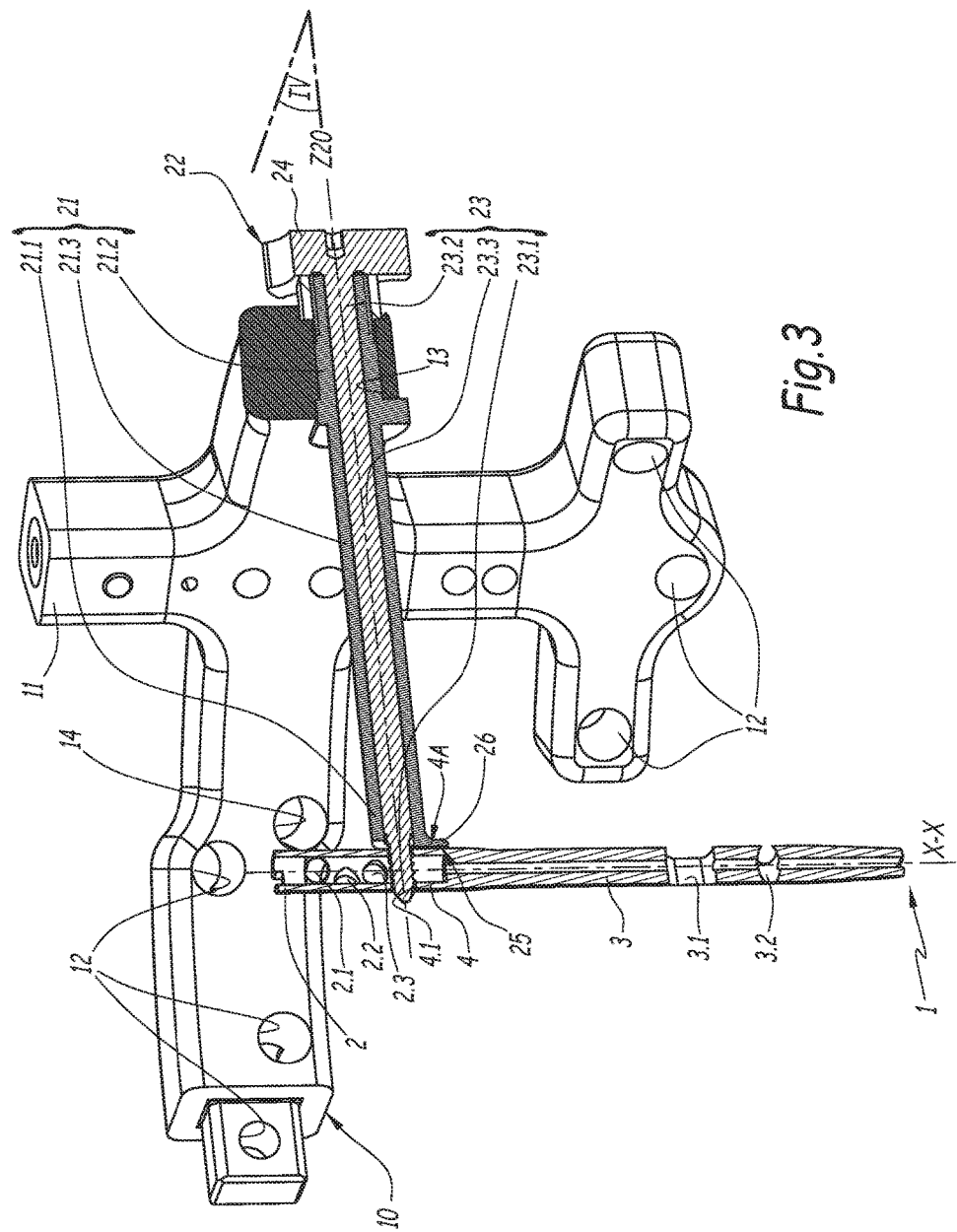
FIG. 3 is a view similar to FIG. 2, with partial sectional view in plane III of FIG. 2.
Figure 4:
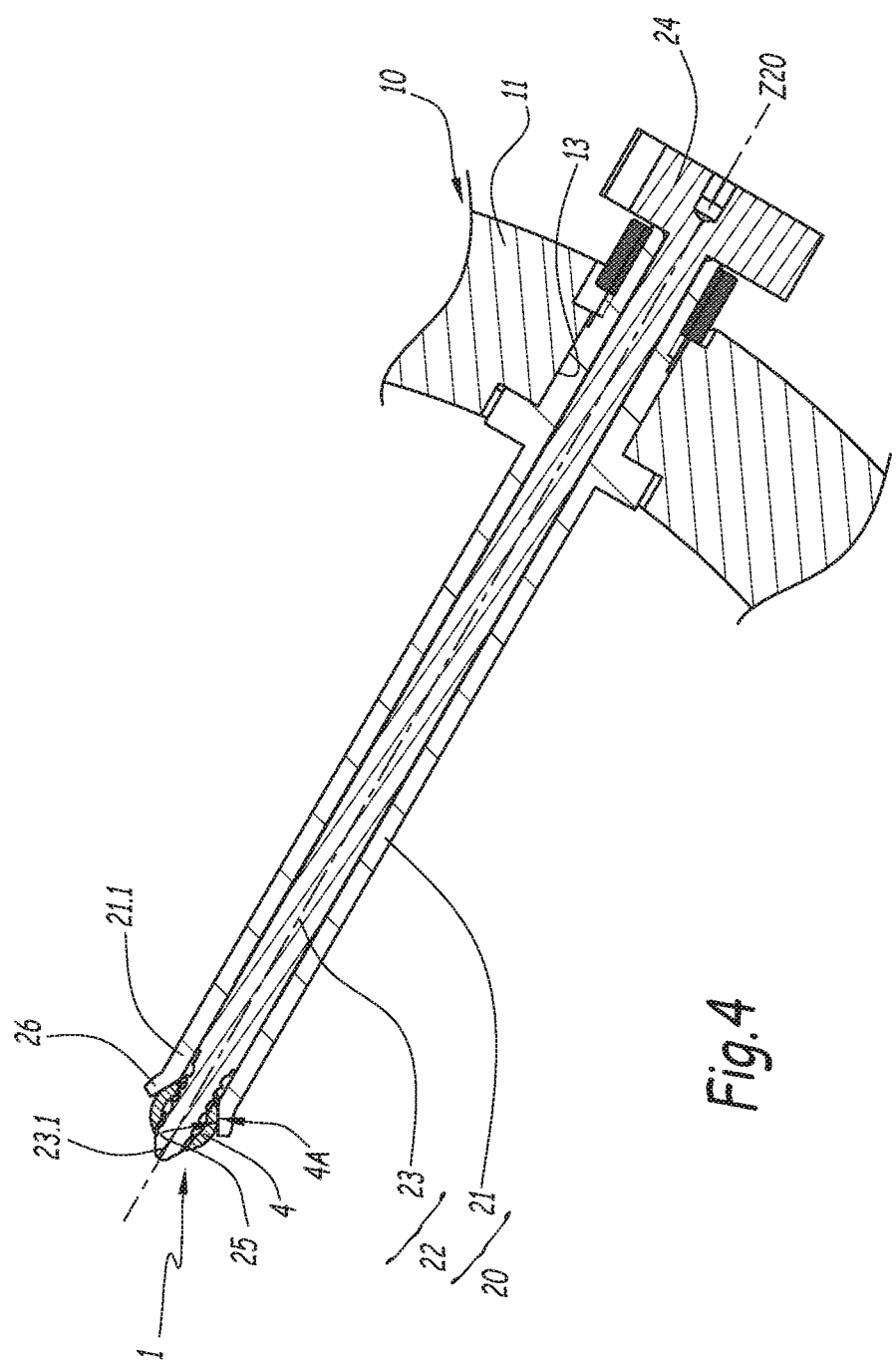
FIG. 4 is a sectional view in plane IV of FIG. 3.

FIGS. 1 to 4 show surgical instrumentation I designed to implant an osteosynthesis nail 1, shown in FIGS. 2 to 4, in a long bone, not shown in FIGS. 1 to 4. Preferably, the instrumentation I allows the implantation in a humerus, the nail 1 then being humeral. Alternatively, the instrumentation I may be provided to implant the nail 1, or a similar osteosynthesis nail, in another long bone, such as the femur or the tibia.

The osteosynthesis nail 1 considered in FIGS. 2 to 4 has an elongated shape, centered on a rectilinear geometric axis X-X. In a manner known in itself, the implantation of the nail 1 consists of placing this nail inside a long bone, causing it to extend lengthwise inside the medullary cavity of the diaphysis of this bone, globally coaxially to this cavity. The outer shape of the nail 1 is adapted accordingly, in a manner known in itself and therefore not described in more detail here.

As clearly shown in FIGS. 2 and 3, the nail 1 includes terminal longitudinal parts 2 and 3, which are opposite one another along the axis X-X and which are separated from one another by a running part 4 of the nail 1. The terminal parts 2 and 3 and the running part 4 are aligned along the axis X-X, thus giving the elongated shape of the implant 1 a rectilinear global profile, inasmuch as none of the parts 2, 3 and 4 are bent relative to the other parts.

For the purposes of transverse fastening between the nail 1 and the bone in which this nail is implanted, the terminal parts 2 and 3 are completely traversed by holes centered on the respective geometric axes that extend transversely, or even perpendicular to the axis X-X. In the example considered here, three of these holes are provided in the terminal part 2, respectively referenced 2.1, 2.2 and 2.3, while two of these holes are provided in the terminal part 3, respectively referenced 3.1 and 3.2. At each of the terminal parts 2 and 3, the corresponding holes 2.1, 2.2 and 2.3, 3.1 and 3.2, respectively, are distributed along the axis X-X, while being centered on the respective geometric axes, which, projected in a plane perpendicular to the axis X-X, are generally oriented differently from one another. The number and orientation of the holes 2.1, 2.2, 2.3, 3.1 and 3.2 are not limiting with respect to the invention. In all cases, each of these holes 2.1, 2.2, 2.3, 3.1 and 3.2 is suitable for receiving a screw or a similar fastening element, not shown in FIGS. 1 to 4, to fasten the nail 1 and the long bone in which this nail is implanted to one another transversely.

The instrumentation I comprises a targeting ancillary tool 10 designed to target the holes 2.1, 2.2, 2.3, 3.1 and 3.2 of the nail 1 percutaneously when this nail is in place in a long bone. To that end, in the example embodiment considered in FIGS. 1 to 4, the targeting ancillary tool 10 comprises a body 11 including a main part 11.1 that has a rectilinear elongated shape intended, during use, to extend globally parallel to the long bone, while being placed, like the rest of the body 11, outside the flesh and the other soft parts surrounding this bone. In its running region, the body part 11.1 is provided with two protruding lateral body parts 11.2 and 11.3, each forming a cradle that, during use, partially surrounds the bone globally orthoradially. Thus, in a cutting plane transverse to the body part 11.1 passing through the body parts 11.2 and 11.3, the body 11 globally has a C-shaped profile. Likewise, in one of its opposite end regions, the body part 11.1 is provided with two other protruding lateral body parts 11.4 and 11.5, each forming a cradle similar to the body parts 11.2 and 11.3, but less extensive than the latter on either side of the body part 11.1. In the scenario where the instrumentation I is used to implant the nail 1 in the humerus, the body 11 is arranged, during use, such that its body part 11.1 extends lengthwise along the corresponding arm of a patient with the insertion of the soft parts of this arm between the humerus and the parts 11.1 to 11.5 of the body 11.

As clearly shown in FIGS. 1 to 3, the body 11 of the targeting ancillary tool 10, in particular each of its body parts 11.1 to 11.5, is provided with through holes 12. These through holes 12 are centered on respective geometric axes Z12 that, when the targeting ancillary tool 10 and the nail 1 are positioned fixedly relative to one another in a predetermined configuration, extend transversely, or even perpendicular, to the axis X-X of the nail 1, while being, for at least some of them, respectively aligned with one of the holes 2.1, 2.2, 2.3, 3.1 and 3.2 of the nail. The axes Z12 of the holes 12 thus respectively constitute targeting axes along which the holes 12 of the body 11 are, during use, oriented toward the nail 1 such that at least some of the targeting holes 12 identify, extra-cutaneously, the holes 2.1, 2.2, 2.3, 3.1 and 3.2 of the nail 1. In practice, each targeting axis Z12 extends at plus or minus 45° from a perpendicular to the axis X-X, or plus or minus 40°, or plus or minus 35°, or plus or minus 30°, or plus or minus 25°, or plus or minus 20°, or plus or minus 15°, or plus or minus 10°, or plus or minus 5° from a perpendicular to the axis X-X, or preferably perpendicularly to the axis X-X.

During use, when the targeting ancillary tool 10 and the nail 1 are positioned fixedly relative to one another in the aforementioned predetermined configuration, the targeting holes 12 whose axes Z12 are aligned with one of the holes 2.1, 2.2, 2.3, 3.1 and 3.2 of the nail 1 make it possible to place, percutaneously and along the axes Z12 of the affected holes 12, screws or similar fastening elements, to fasten the nail 1 and the long bone in which this nail is placed to one another transversely. To that end, as will be described later, each of the targeting holes 12 is designed to inwardly receive a tubular sleeve, which extends in a centered manner along the corresponding axis Z12 and the inside of which guides the aforementioned screw, or the similar fastening element, into one of the holes 2.1, 2.2, 2.3, 3.1 and 3.2 so that this screw or this fastening element can engage the nail with the bone in which the nail is housed.

In the example embodiment considered in FIGS. 1 to 4, the targeting ancillary tool 10 has more targeting holes 12 than there are holes 2.1, 2.2, 2.3, 3.1 and 3.2 of the nail 1. This is explained by the fact that the targeting ancillary tool 10 is advantageously designed to be associated with at least two different nails, this ancillary tool being used to implant either of these two different nails interchangeably. In particular, the targeting ancillary tool 10 is advantageously designed to be used interchangeably with a nail to be implanted in a left long bone and with a nail to be implanted in a right long bone: in the scenario of an implantation in the humerus, the targeting ancillary tool 10 makes it possible to implant a left humeral nail and a right humeral nail interchangeably. In this case, the body 11 and the targeting holes 12 are distributed symmetrically on either side of the geometric plane, denoted P in FIG. 2, on either side of which the body parts 11.2 and 11.3 are symmetrical with respect to one another and the body parts 11.4 and 11.5 are symmetrical with respect to one another.

The instrumentation I further comprises means 20 suitable for fastening the ancillary tool 10 and the nail 1 to one another in the aforementioned predetermined configuration. These fastening means 20, which are shown in FIGS. 1 to 4, define a fastening axis Z20 that, during use, extends transversely, or even perpendicular to the nail 1. In practice, the fastening axis Z20 extends at plus or minus 45° from a perpendicular to the axis X-X, or plus or minus 40°, or plus or minus 35°, or plus or minus 30°, or plus or minus 25°, or plus or minus 20°, or plus or minus 15°, or plus or minus 10°, or plus or minus 5° from a perpendicular to the axis X-X, or preferably perpendicularly to the axis X-X.

In the embodiment considered in FIGS. 1 to 4, the fastening means 20 comprises a bar 21 that extends lengthwise along the fastening axis Z20 and that is designed to connect the body 11 of the targeting ancillary tool 10 and the nail 1 to one another. This bar 21 includes:

a distal end 21.1, which, as clearly shown in FIGS. 2 to 4, is arranged, along the axis X-X, at the running part 4 of the nail 1 in order to cooperate with this running part 4, as explained hereinafter;

a proximal end 21.2, which, along the axis Z20, is opposite the distal end 21.1 and which, during use, provides a fixed connection between the rest of the bar 21 and the body 11 of the targeting ancillary tool 10; and a running part 21.3 connecting the distal 21.1 and proximal 21.2 ends to one another along the axis Z20.

The proximal end 21.2 of the part 21 is received and fixedly blocked in a complementary hole 13 defined by the body 11 of the targeting ancillary tool 10. During use, the proximal end 21.2 of the bar 20 and the hole 13 of the targeting ancillary tool 10 cooperate such that the part 21 is fixedly supported by the targeting ancillary tool. In practice, the embodiment for this cooperation between the proximal end 21.2 of the bar 21 and the hole 13 of the targeting ancillary tool 10 is not limiting. According to one advantageous optional arrangement, which is implemented in the embodiment of FIGS. 1 to 4, the fixed connection between the bar 21 and the targeting ancillary tool 10 is removable, such that, when not in use, the bar 21 can be disengaged from the body 11 of the targeting ancillary tool 10, for example for storage and/or cleaning purposes. This option further makes it possible to interchange the arrangement of the part 21 on the targeting ancillary tool 10, as long as the body 11 of the latter defines, in addition to the aforementioned hole 13, another hole 14 for receiving and fixedly blocking the proximal end 21.2 of the bar 21: in the example embodiment considered in FIGS. 1 to 4, the holes 13 and 14 are respectively defined in the body parts 11.2 and 11.3, symmetrically relative to the plane P, such that the targeting ancillary tool 10 makes it possible to support the bar 21 interchangeably between two symmetrical regions of its body 11 depending on whether this targeting ancillary tool was used with a left nail or a right nail, as mentioned above.

The fastening means 20 also comprise a mechanism 22 making it possible both to rigidly connect the bar 21 to the nail 1, by connecting laterally to this nail, and to guide the relative positioning between the bar 21 and the nail 1 to the aforementioned predetermined configuration.

As clearly shown in FIGS. 3 and 4, the mechanism 22 includes a rod 23, which extends lengthwise along the fastening axis Z20 and which is received, coaxially and movably, inside the bar 21. The rod 23 includes a distal part 23.1 that, during use, emerges from the distal end 21.1 of the bar 21. Opposite this distal part 23.1 along the axis Z20, the rod 23 includes a proximal part 23.2 that, during use, emerges from the proximal end 21.2 of the part 21, thus traversing the hole 13 to emerge from the body 11 of the targeting ancillary tool 10 on the side of this body 11, opposite the running part 21.3 of the bar 21. The proximal end 23.2 of the rod 21 is provided with a wheel 24 for actuating the rod 23, allowing the user of the instrumentation I to move the rod 23 inside the bar 21. The rod 23 further includes a running part 23.3 rigidly connecting the distal 23.1 and proximal 23.2 parts to one another.

The distal part 23.1 of the rod 23 is designed to be rigidly connected to the running part 4 of the nail 1. To that end, in the embodiment considered here, the distal part 23.1 is threaded, as clearly shown in FIG. 1, such that during use, the threaded part 23.1 can be screwed into a complementary tapping defined by a through hole 4.1 of the running part 4 of the nail 1, as shown in FIGS. 2 to 4. It will be understood that, during use, when the targeting ancillary tool 10 and the nail 1 are positioned in the aforementioned predetermined configuration, the axis of the tapped hole 4.1 is aligned with the fastening axis Z20, such that, by rotating the rod 23 around itself around the axis X20, via its proximal wheel 24, the distal part 23.1 of the rod 23 is gradually screwed into the tapping of the hole 4.1, advantageously until it emerges partially from this hole, on the side of the running part 4 opposite that turned toward the part 21. In other words, the distal part 23.1 of the rod 23 is designed here to traverse, along the axis Z20, the running part 4 of the nail 1 completely, while screwing itself therein.

The connecting mechanism 22 also includes a surface 25 that, by contact with the lateral surface 4A of the running part 4 of the nail 1, guides the positioning of the nail 1 into the aforementioned predetermined configuration. This positioning guiding surface 25 is fixedly supported by the bar 21. In the embodiment considered here, this surface 25 is defined directly by the distal end 21.1 of the bar 21, the distal end 21.1 advantageously being configured in a tube portion 26, which is centered on an axis perpendicular to the fastening axis Z20 and which inwardly forms a positioning guiding surface 25, as clearly shown in FIGS. 3 and 4: this tube portion 26 gives the surface 25 a V-shaped profile that stabilizes the nail 1 during use, by covering a portion of the surface 4A of the running part 4 of the nail by the surface 25. Due to its V-shaped profile, this surface 25 thus has two planar facets that grip the aforementioned portion of the surface 4A between them.

Based on the preceding explanations, it will be understood that the bar 21 and the mechanism 22 cooperate with the running part 4 of the nail 1 to thus fasten the targeting ancillary tool 10 to the nail 1 along the fastening axis Z20, i.e., to fasten this targeting ancillary tool to the nail 1 laterally. In particular, the bar 21 and the mechanism 22 cooperate exclusively with the running part 4 of the nail 1, without interacting with the terminal parts 2 and 3 of this nail, thereby making it possible to fasten the ancillary tool 10 exclusively laterally to the nail 1.

As shown only in FIG. 1, the instrumentation I optionally comprises a system 30 for retro-impacting the nail 1. This system 30 includes a casing 31 able to be rigidly connected, advantageously removably, to the body 11 of the targeting ancillary tool 10. In the example considered here, the casing 31 is designed to be screwed to one of the longitudinal ends of the body part 11.1, provided to that end with a complementary tapping. The retro-impacting system 30 further includes a flyweight 32 mounted movably inside the casing 31: by moving the flyweight 32 inside the casing 31, the flyweight abuts against the casing and thus strikes, via the latter, the targeting ancillary tool 10. During use, when the targeting ancillary tool 10 is fastened to the nail 1 using the fastening means 20, the impacts resulting from the striking of the targeting ancillary tool by the flyweight 32 are transmitted [from] the targeting ancillary tool to the nail 1 via the fastening means 20.

We will now describe, more specifically in light of FIGS. 5 to 10, an example of a surgical method using the instrumentation I, to implant the nail 1.

Figure 5:
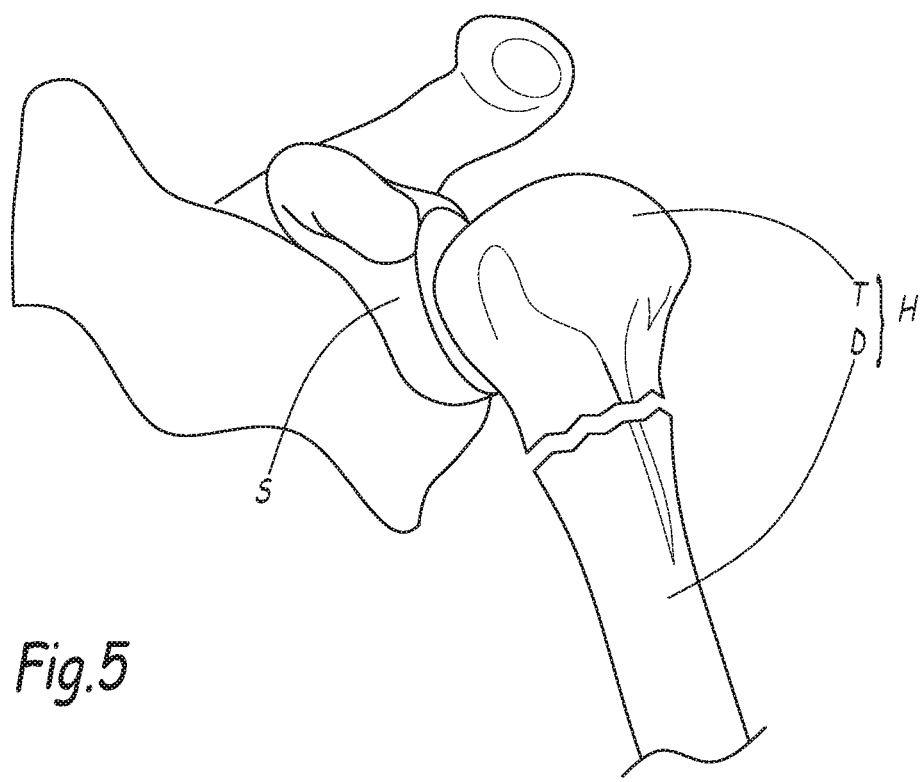
FIG. 5 is a perspective view of a shoulder blade and a humerus fractured between its head and its diaphysis.

As shown in FIG. 5, this method is implemented on a humerus H that is fractured between its head T, in other words its proximal end, and its diaphysis D. The corresponding fracture is said to have two fragments, inasmuch as the head T and the diaphysis D respectively constitute single-piece fragments, separated from one another by the fracture. Of course, in practice, small bone debris, resulting from the fracture, may be present between the head T and the diaphysis D, this debris being evacuated at the beginning of the surgical procedure seeking to reduce the fracture. The shoulder blade associated with the humerus H is referenced S in FIG. 5.

During the surgical procedure, the surgeon opens an approach by making an incision in the soft flesh of the arm of the patient undergoing the operation. This incision is done transversely to the humerus H, at its fracture between the head T and the diaphysis D. In practice, this approach is preferably deltopectoral. Alternatively, it may be superolateral. In all cases, the surgeon views the fracture site directly through the approach thus opened.

The instrumentation I is made available in its configuration shown in FIGS. 2 to 4, i.e., in the aforementioned predetermined configuration, in which the targeting ancillary tool 10 is fastened to the nail to the implanted 1 via the fastening means 20. To that end, while the bar 21 is fastened to the body 11 of the targeting ancillary tool 10 and the distal part 23.1 of the rod 23 does not substantially emerge from the distal end 21.1 of the bar 21, the nail 1 is positioned at the distal end 21.1 of the bar 21 such that the hole 4.1 of its running part 4 is aligned on the axis X20. The user then manipulates the wheel 24 to drive the rod 23 both in rotation around the axis Z20 and in translation along this axis, so as to screw the distal part 23.1 of this rod through the running part 4 of the nail 1, in the hole 4.1 of this running part 4. This screwing tends to gradually bring the running part 4 of the nail 1 and the distal end 21.1 of the part 21 closer to one another along the axis Z20, until the lateral surface 4A of the running part 4 is in contact with the surface 25 defined at the distal end 21.1 of the bar 21. By contact cooperation between these surfaces 4A and 25, the bar 21 and the nail 1 are, over the course of the screwing of the rod 23 through the running part 4 of the nail 1, guided in position relative to one another, until the targeting ancillary tool 10 and the nail 1 are positioned fixedly in the aforementioned predetermined configuration.

Figure 6:
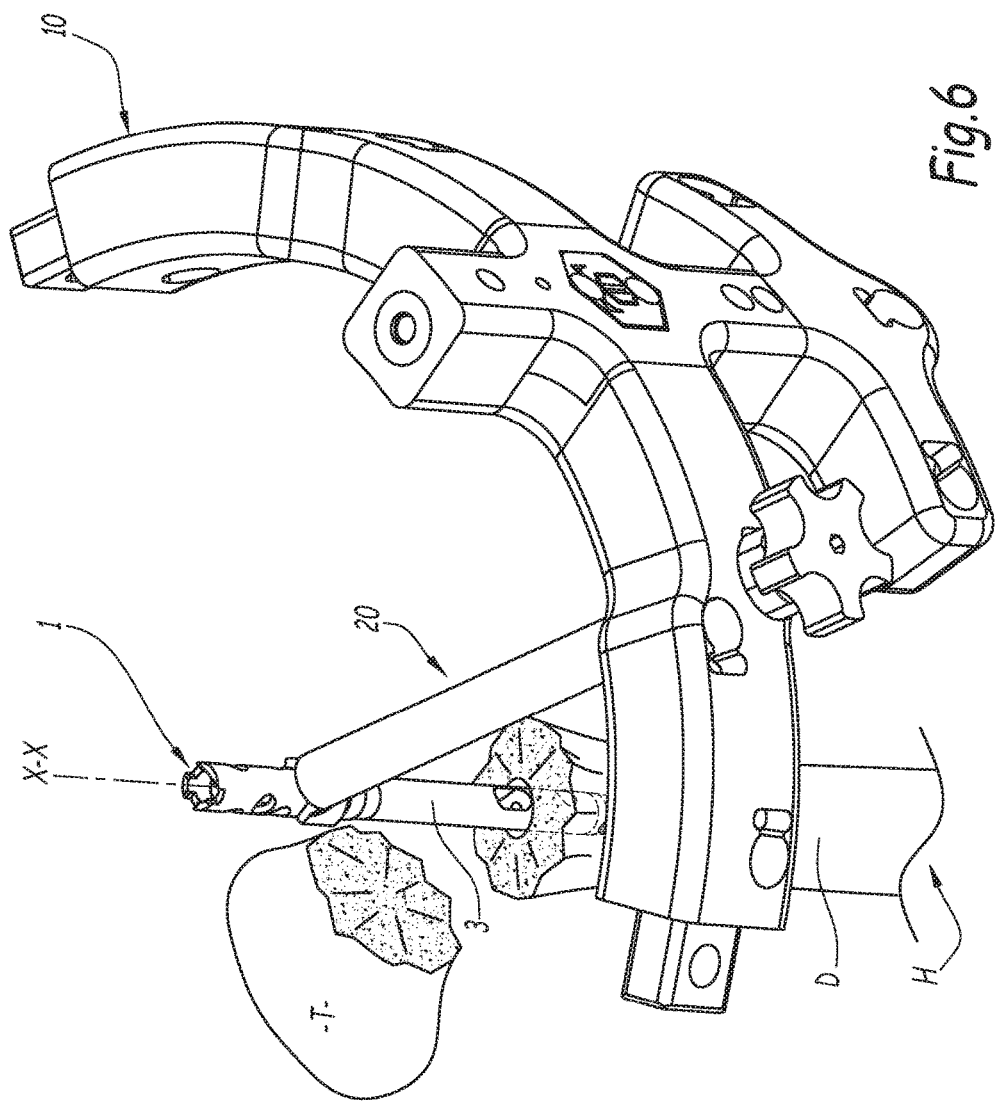
FIGS. 6 to 9 are perspective views illustrating successive steps of a use of the instrumentation of FIG. 1 to implant the nail of FIG. 2 in the humerus of FIG. 5.

The targeting ancillary tool 10 is next manipulated by the surgeon so as to insert the terminal part 3 of the nail 1, fastened to this targeting ancillary tool by the fastening means 20, to the inside of the medullary cavity of the diaphysis D, as shown in FIG. 6.

This insertion of the nail 1 into the medullary cavity of the diaphysis D is done via the surgical approach previously opened, the head T of the humerus H being separated from the diaphysis D enough not to hinder this insertion. The surgeon next positions the terminal part 3 of the nail 1 appropriately inside the medullary cavity of the diaphysis D, by direct observation by the surgeon through the incision of the approach. In particular, perioperative fluoroscopy is advantageously not necessary.

Figure 7:
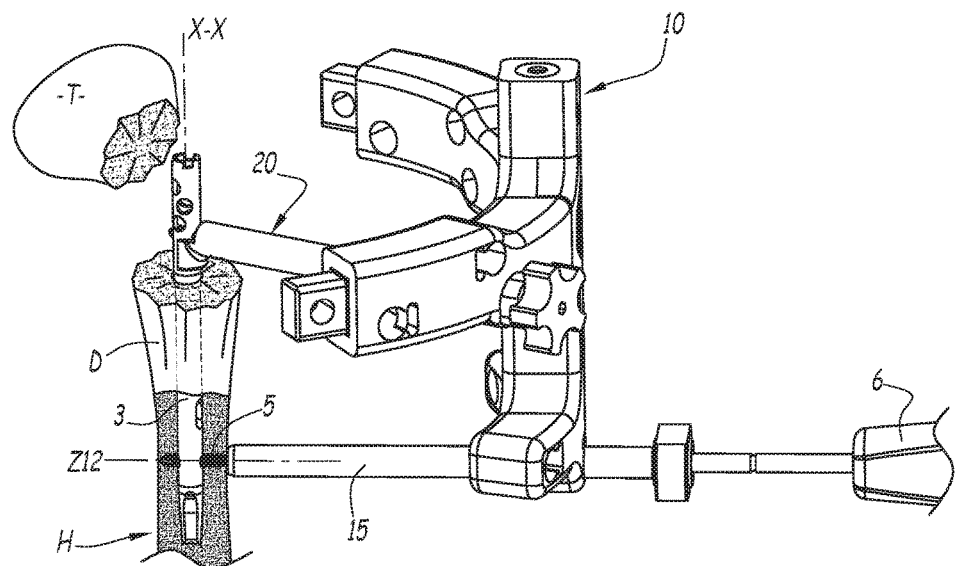

Then, the surgeon uses the targeting ancillary tool 10 to place one or several transverse fastening screws 5 between the diaphysis D and the terminal part 3 of the nail 1, as shown in FIG. 7. To that end, for each of the screws 5 to be placed, a sleeve 15 is attached in one of the targeting holes 12 of the body 11 such that this sleeve 15 guides, percutaneously and along the axis Z12 of the affected hole, the screw 5 from the hole 12 to the affected hole 3.1 and 3.2. In practice, the surgeon uses an ad hoc tool 6 allowing him to drive the screw 5 from the side of the body 11, opposite the humerus H. Once the screw(s) 5 are placed, it is understood that the terminal part 3 of the nail 1 is fixedly connected to the diaphysis D.

Figure 8:
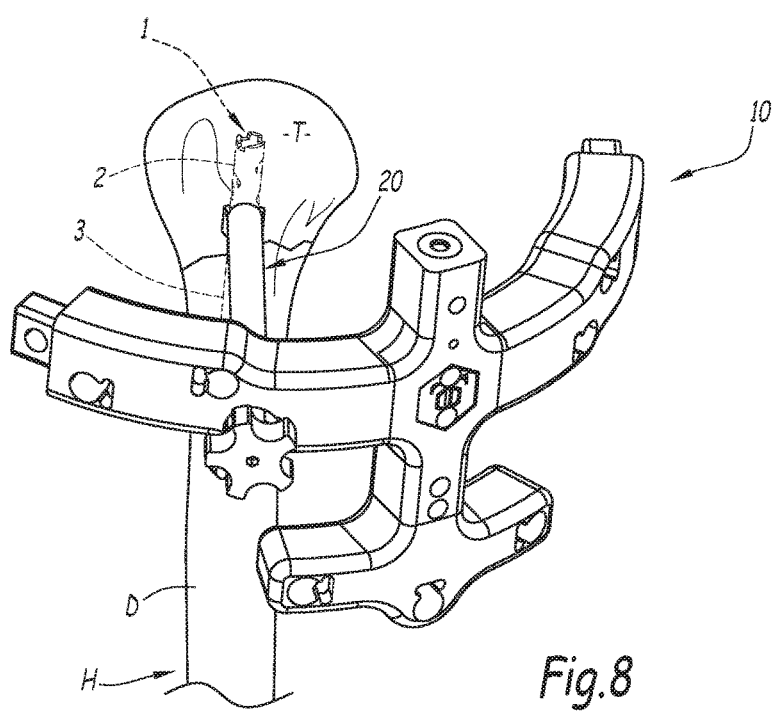

As shown in FIG. 8, the surgeon next replaces the head T in the longitudinal extension of the diaphysis D, manipulating the latter via the aforementioned approach. As shown in FIG. 8, the fracture is thus reduced by butting the diaphysis D and the head T, while allowing the fastening means 20 to pass between them. The terminal part 2 of the nail 1 is thus housed inside the head T.

Figure 9:
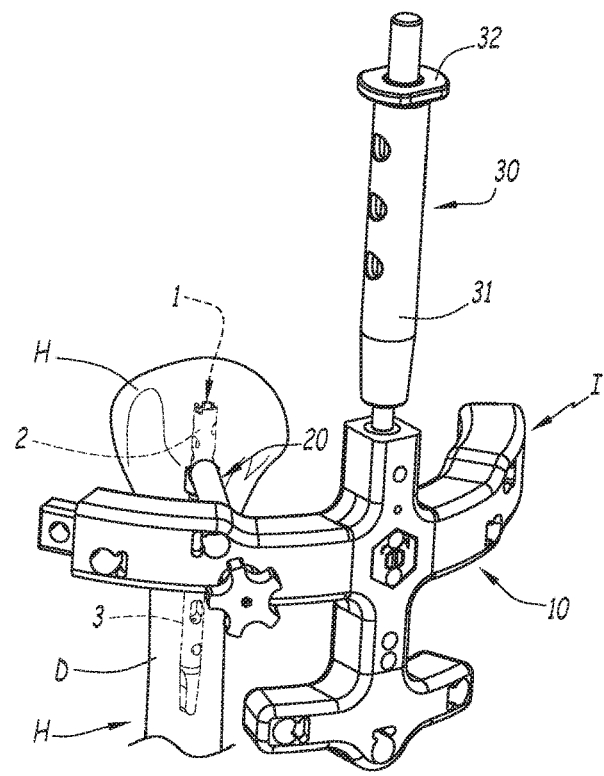

If necessary, and as long as the head T allows it, in particular by forming a single-piece fragment, the surgeon next retro-impacts the terminal part 2 of the nail 1 inside the head T using the retro-impaction system 30 previously attached on the targeting ancillary tool 10, as shown in FIG. 9: by striking the targeting ancillary tool 10 via the flyweight 32, the surgeon applies impacts on the nail 1, via the fastening means 20, that tend to press the terminal part 2 of the nail 1 inside the head T and thus forcibly position this head with respect to the nail 1.

Figure 10:
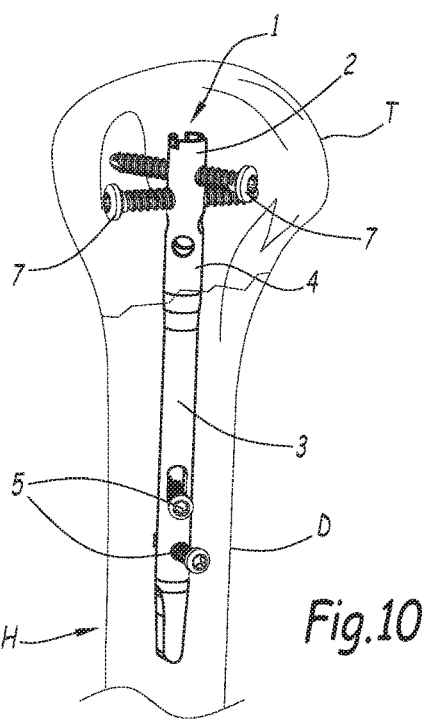
FIG. 10 is a perspective view of the humerus of FIG. 5, after implantation of the nail of FIG. 2 using the instrumentation of FIG. 1.

Once the head T is suitably positioned on the terminal part of the nail 1, the surgeon uses the targeting ancillary tool 10 to place one or several transverse fastening screws 7 between the head T and the terminal part 2 of the nail 1. According to considerations similar to those developed above for the screws 5, each of the screws 7 is received in one of the holes 2.1 to 2.3 of the terminal part 2, targeting this hole via one of the holes 12 of the body 11 and using the sleeve 15 to guide this screw 7 percutaneously along the axis Z12 of the affected hole 12. The targeting ancillary tool 10 can next be disengaged from the nail 1, subject to the release of the fastening means 20: to do this, the surgeon unscrews the rod 23 to release the running part 4 of the nail 1 therefrom. The humerus H and the nail 1 are then as shown in FIG. 10.

The surgeon lastly closes the approach.

Various alternatives of the example surgical method described above can be considered. One of them relates to the case of a fracture of the humerus H with more than two fragments. In particular, when the head H itself is fractured in several fragments, the surgeon may, after fastening the diaphysis D to the terminal part 3 of the nail 1, unite these fragments of the head around the terminal part 2 of the nail 1, thereby reducing the fracture lines between the different fragments of the humerus H; next, the surgeon may either keep at least some of the fragments of the head in position by suturing them together, via the approach, before placing the fastening screws 7 by using the targeting ancillary tool 10, or, if one or at least some of the fragments of the head allow it, fasten each of these fragments to the terminal part 2 by at least as many screws 7 as there are fragments.

Furthermore, the method described above may, in alternatives that are not shown, be implemented for long bones other than the humerus, in particular the femur and tibia. The instrumentation I thus makes it possible to implant a femoral nail in a fractured femur at least between its head, in other words, its proximal end, and its diaphysis, as well as to implant a tibial nail in a fractured tibia at least between its proximal end and its diaphysis.

Figure 11:
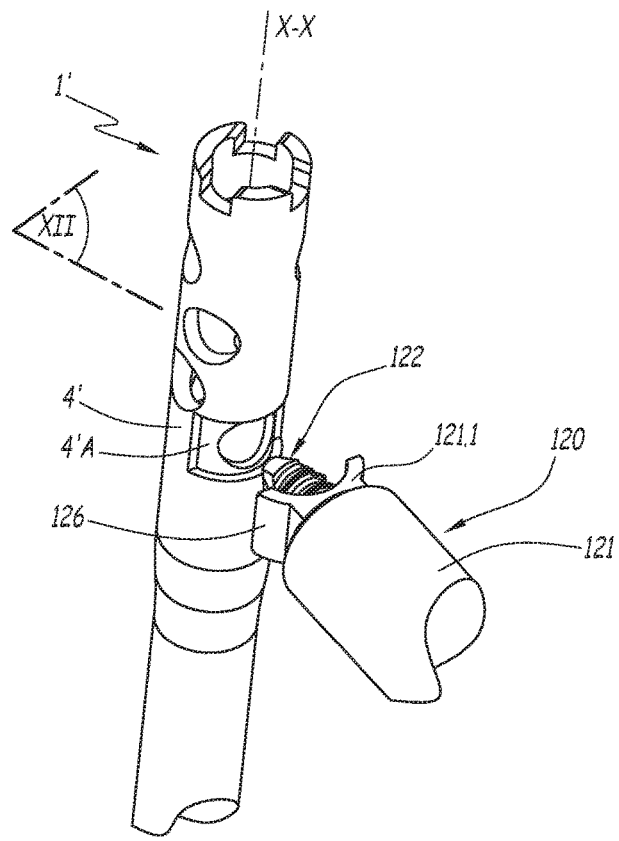
FIG. 11 is a perspective view of a second embodiment of the instrumentation, associated with an osteosynthesis nail.
Figure 12:
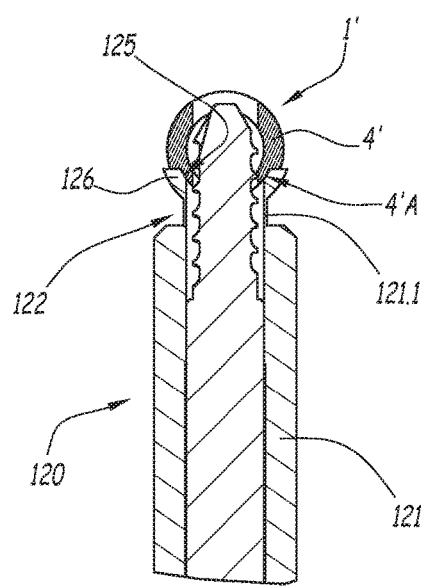
FIG. 12 is a sectional view in plane XII of FIG. 11, the instrumentation being in a different usage state from that of FIG. 11.

FIGS. 11 and 12 show a second embodiment of the instrumentation I, having fastening means 120 that comprise a bar 121 and a mechanism 122, which are functionally similar to the bar 21 and the mechanism 22 of the means 20 of the instrumentation of FIGS. 1 to 4. The mechanism 122 differs from the mechanism 22 in that its positioning guiding surface 125 has a C-shaped transverse profile, defined by a tube portion 126 making up the distal end 121.1 of the bar 121. Furthermore, the running part 4' of the nail 1' associated with this embodiment of the instrumentation I defines, in a hollow in its lateral surface 4'A, an additional receiving housing for the tube portion 126. Thus, during use, as shown in FIG. 12, the distal end 121.1 of the bar 121 is partially received inside the housing hollowed in the lateral surface 4'A of the running part 4' of the nail 1', the C-shaped profile of the surface 125 completely covering the bottom of this housing in an adjusted manner. The stabilization of the nail 1' by the fastening means 120 when the latter fasten the nail to the targeting ancillary tool is reinforced as a result. Of course, the implementation of this alternative embodiment requires a specific development of the running part 4' of the nail 1', unlike the instrumentation of FIGS. 1 to 4, which can be implemented with a nail not having any development of its lateral surface, or even with a pre-existing nail subject to the presence of a tapped hole similar to the hole 4.1.

Figure 13:
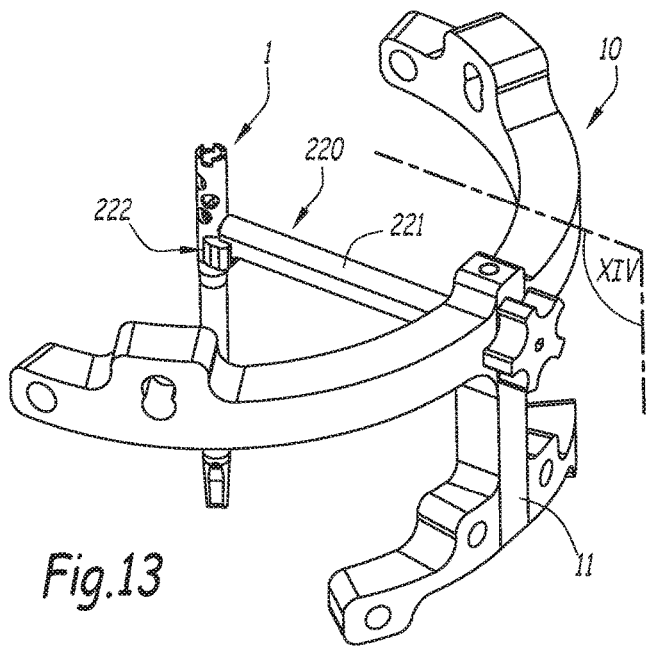
FIG. 13 is a perspective view of a third embodiment of instrumentation, associated with an osteosynthesis nail.
Figure 14:
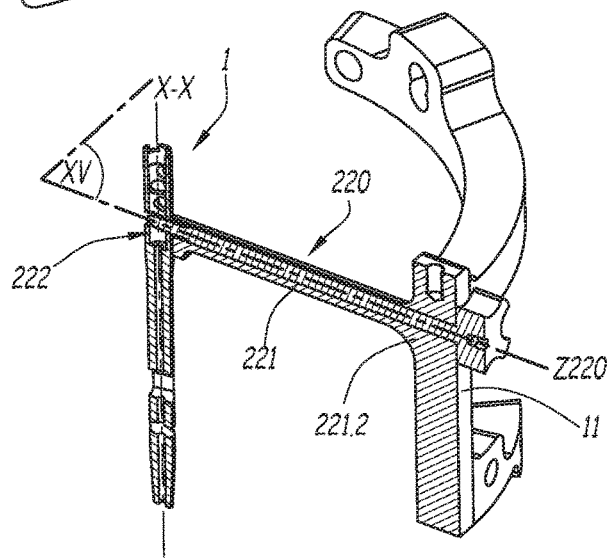
FIG. 14 is a view similar to FIG. 13, with a partial sectional view along plane XIV of FIG. 13.
Figure 15:
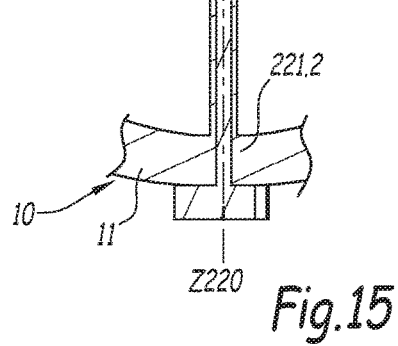
FIG. 15 is a sectional view in plane XV of FIG. 14.

FIGS. 13 and 15 show a third embodiment of the instrumentation I, having fastening means 220 that comprise a bar 221 and a mechanism 222, which are functionally similar to the bar 21 and the mechanism 22 of the means 20 of the instrumentation of FIGS. 1 to 4. The bar 221 differs from the bar 21 in that it is permanently secured to the targeting ancillary tool 10, while for example being integral with the body 11 of this targeting ancillary tool. In other words, the body 11 and the bar 221 are monolithic, or more generally, form a single-piece assembly. In this case, the fastening axis Z220 of the fastening means 220 is situated in the plane of symmetry P of the targeting ancillary tool 10 and the proximal end 221.2 of the bar 221 is secured with, or even formed by the part of the median body of the body 11 of the targeting ancillary tool.

Figure 16:
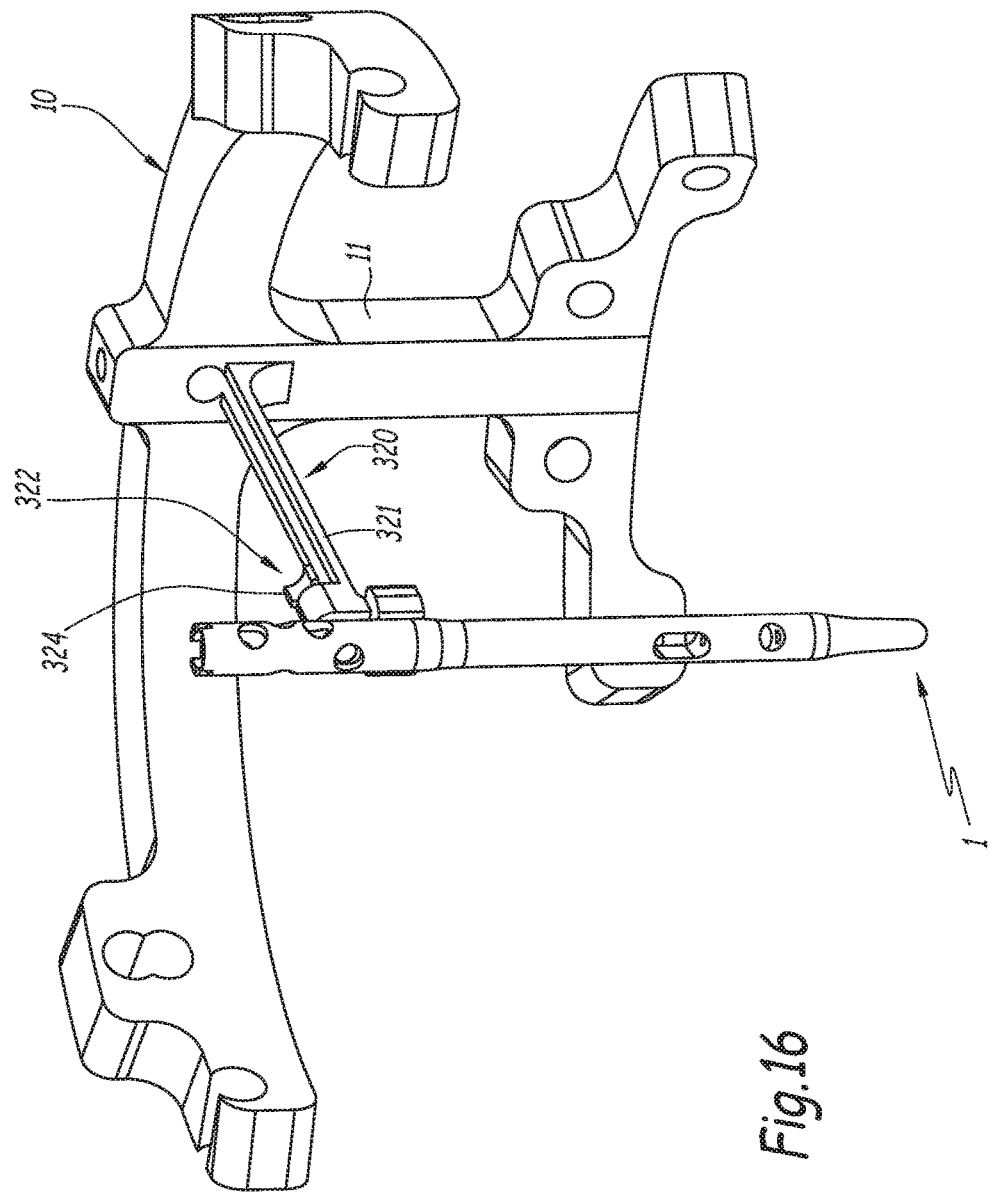
FIG. 16 is a perspective view of a fourth embodiment of the instrumentation, associated with an osteosynthesis nail.

FIG. 16 shows a fourth embodiment of the instrumentation I, having fastening means 320 that comprise a bar 321 and a mechanism 322, which are functionally similar to the bar 21 and the mechanism 22 of the means 20 of the instrumentation of FIGS. 1 to 4. Like the bar 21, the bar 321 is permanently secured to the body 11 of the targeting ancillary tool 10. The mechanism 322 differs from the mechanism 222 in that the rod of the mechanism 322 is shorter, such that the wheel 324, which, similarly to the wheel 24 previously described, serves to actuate the rod of the mechanism 322, is situated at the running part of the bar 321.

Figure 17:
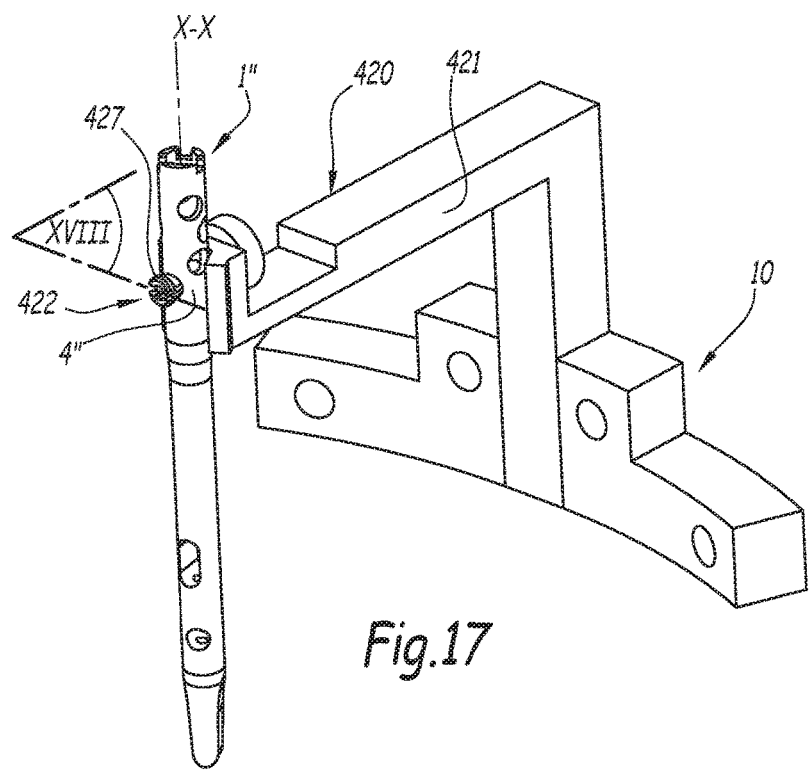
FIG. 17 is a perspective view of a fifth embodiment of the instrumentation, associated with an osteosynthesis nail.
Figure 18:
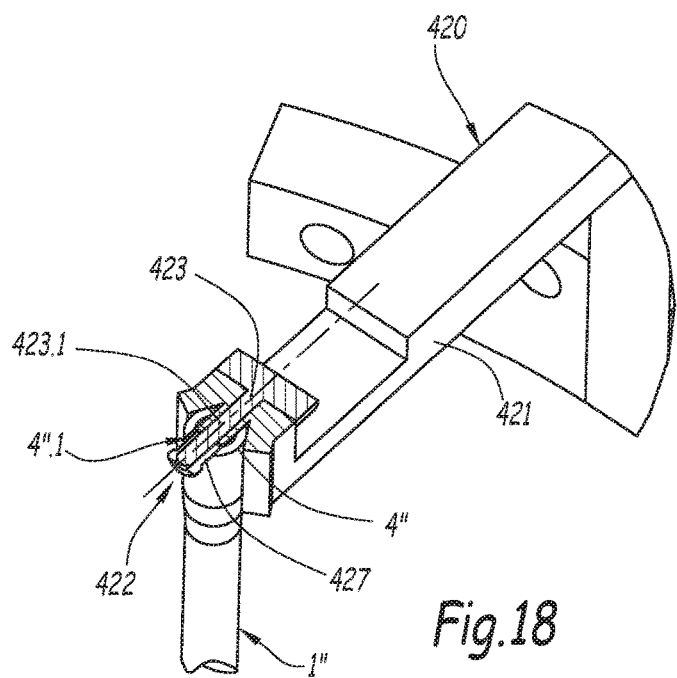
FIG. 18 is a view similar to FIG. 17, with a partial sectional view along plane XVIII of FIG. 17.

FIGS. 17 and 18 show a fifth embodiment of the instrumentation I, having fastening means 420 that comprise a bar 421 and a mechanism 422, which are functionally similar to the bar 21 and the mechanism 22 of the fastening means 20 of the instrumentation of FIGS. 1 to 4. Like for the fastening means 320, the bar 421 is permanently secured to the body 11 of the targeting ancillary tool 10 and the rod 423 of the mechanism 422 is short. Furthermore, unlike the distal part 23.1 of the rod 23, designed to be screwed directly into the hole 4.1 of the running part 4 of the nail 1, the distal part 423.1 of the rod 423 is designed to be screwed into a pin 427 of the mechanism 422: during use, this pin 427 is placed in a complementary through hole 4".1 of the running part 4" of the nail 1", and, as the distal part 423.1 of the rod 423 progresses inside the pin 427 in the direction opposite the bar 421, this pin expands, thus rigidly connecting the distal part 423.1 of the rod 423 to the nail 1".

Figure 19:
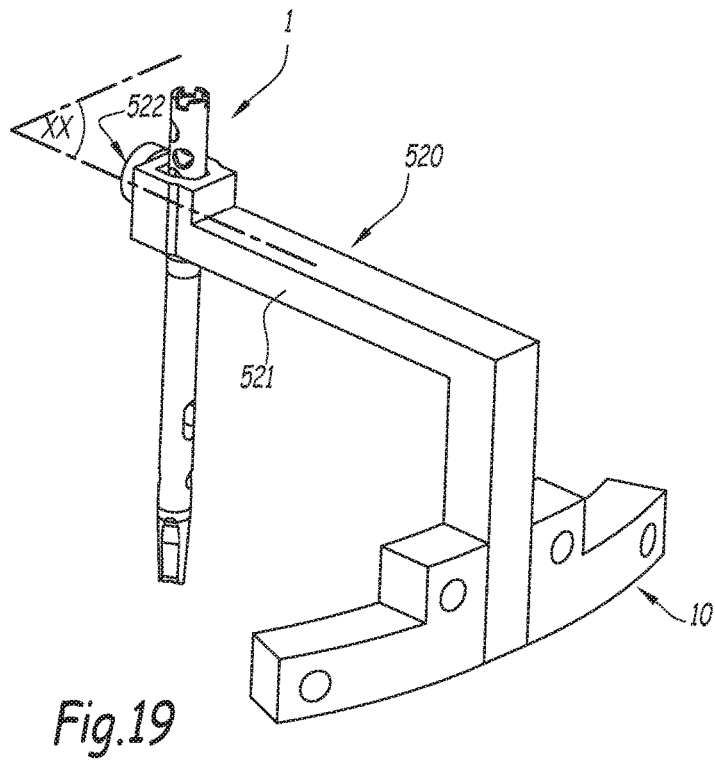
FIG. 19 is a perspective view of a sixth embodiment of instrumentation, associated with an osteosynthesis nail.
Figure 20:
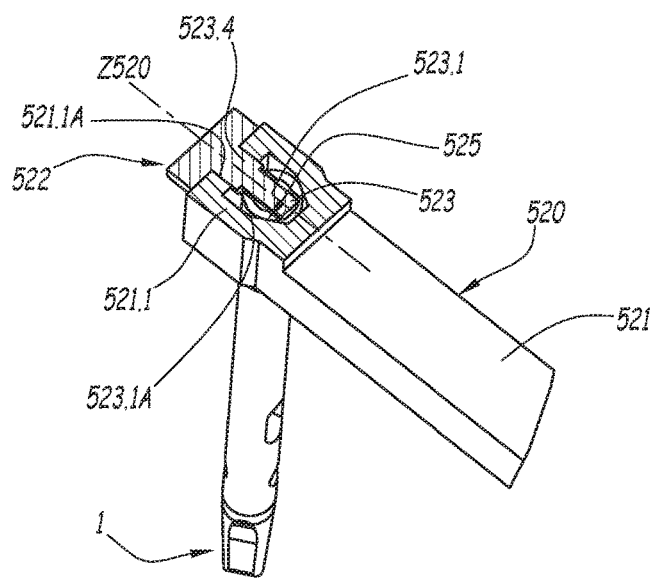
FIG. 20 is a view similar to FIG. 19, with a partial sectional view along plane XX of FIG. 19.

FIGS. 19 and 20 show a sixth embodiment of the instrumentation I, having fastening means 520 that comprise a bar 521 and a mechanism 522, which are functionally similar to the bar 21 and the mechanism 22 of the fastening means 20 of the instrumentation of FIGS. 1 to 4. The rod 523 of the mechanism 522 differs from the rod of mechanism 322 in that the distal part 523.1 of this rod 523 does not cooperate by screwing with the hole 4.1 of the running part 4 of the nail 1, but has a shoulder 523.1A forming a bearing stop to press laterally on the surface 4A of the running part 4 of the nail 1 when the rest of this distal part 523.1 is received in the hole 4.1. Furthermore, this distal part 523.1 the rod 523 extends, along the fastening axis Z520 and opposite the bar 521, by a part 523.4 for screwing the rod 523 into a tapped hole 521.1A defined by the distal end 521.1 of the bar 521: when this part 523.4 is screwed in the distal end 521.1 of the bar 521, the shoulder 523.1A of the distal part 523.1 of the rod 523 comes closer, along the axis Z520, to the surface 4A of the running part 4 of the nail 1, until it presses this running part 4 of the nail laterally, by bearing against its surface 4A whereof the portion, opposite the shoulder 523.1A, is covered by the positioning guiding surface 525 of the mechanism 522.

Figure 21:
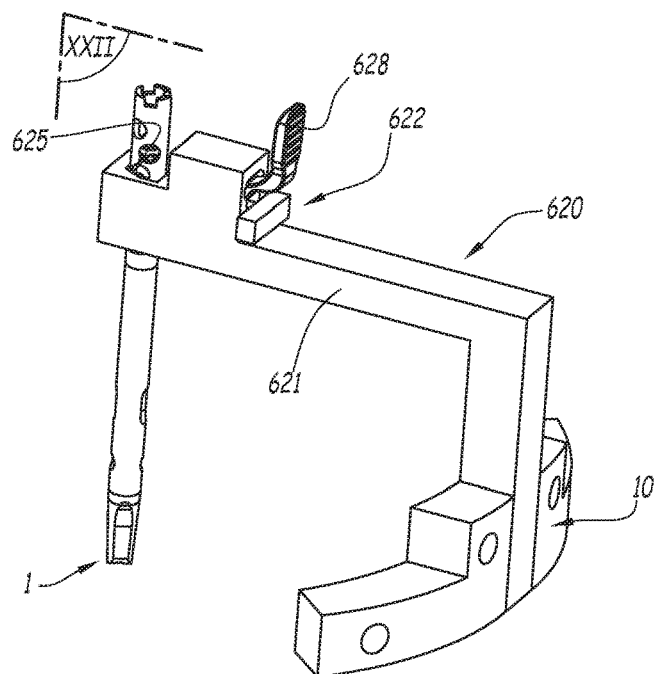
FIG. 21 is a perspective view of a seventh embodiment of the instrumentation, associated with an osteosynthesis nail.
Figure 22:
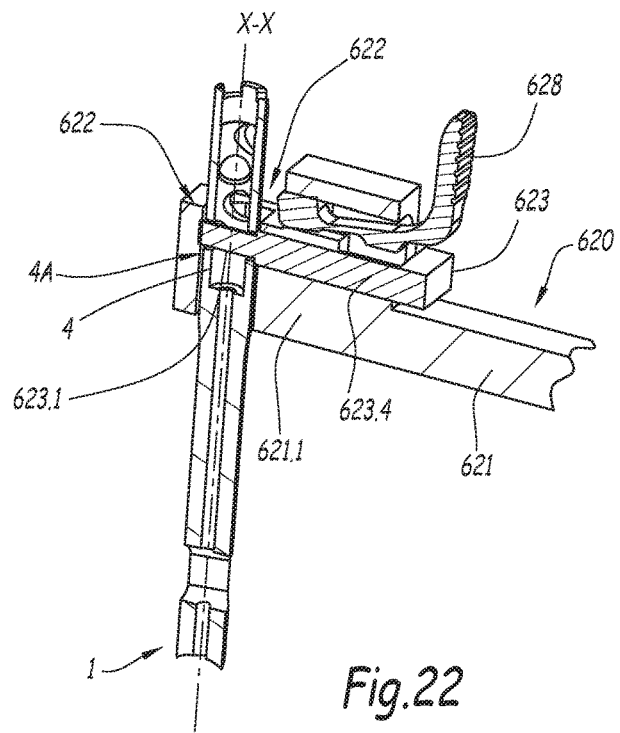
FIG. 22 is a view similar to FIG. 21, with a partial sectional view along plane XXII of FIG. 21.

FIGS. 21 and 22 show a seventh embodiment of the instrumentation I, having fastening means 620 that comprise a bar 621 and a mechanism 622, which are functionally similar to the bar 21 and the mechanism 22 of the means 20 of the instrumentation of FIGS. 1 to 4. Like the mechanism 522, the rod 623 of the mechanism 622 is designed, at its distal part 623.1, to abut bearing against the surface 4A of the running part 4 of the nail 1, so as to press this running part laterally opposite its portion covered by the positioning guiding surface 625 of the mechanism 622. Rather than being screwed into the distal end of the bar, a part 623.4 of the rod 623 is engaged with the distal end 621.1 of the bar 621 by an arm 628 designed to act as a buttress between this part 623.4 of the rod 623 and the distal end 621.1 the bar 621.

Figure 23:
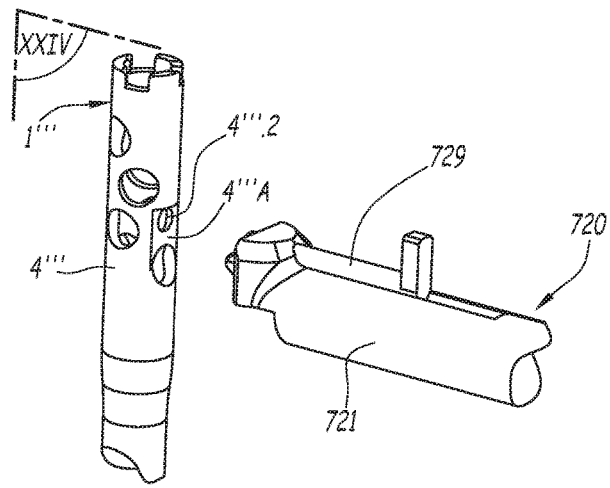
FIG. 23 is a perspective view of an eighth embodiment of instrumentation, associated with an osteosynthesis nail.
Figure 24:
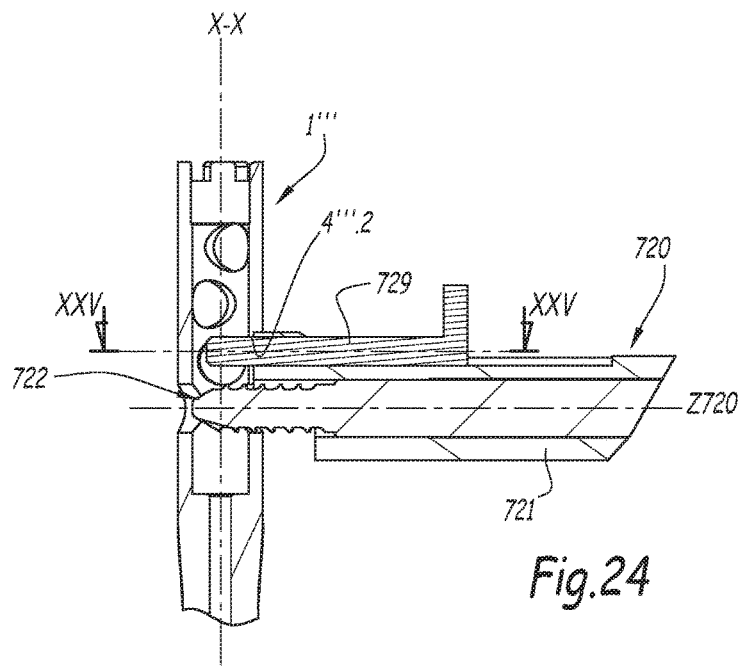
FIG. 24 is a sectional view in plane XXIV of FIG. 23, the instrumentation being shown in a different operating state from that of FIG. 23.
Figure 25:
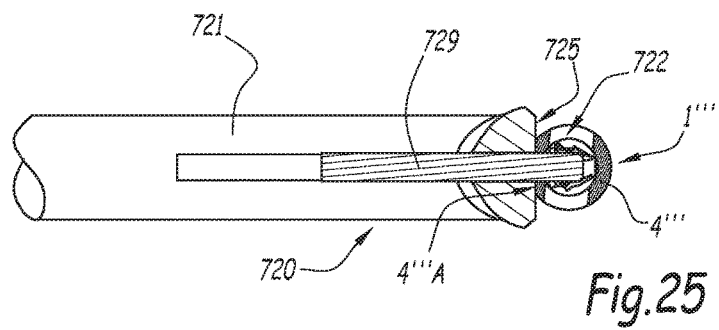
FIG. 25 is a cross-section along line XXV-XXV in FIG. 24.

FIGS. 23 and 25 show an eighth embodiment of the instrumentation I, having fastening means 720 that comprise a bar 721 and a mechanism 722, which are functionally similar to the bar 21 and the mechanism 22 of the fastening means 20 of the instrumentation of FIGS. 1 to 4. The positioning guiding surface 725 of the mechanism 722 differs from the surface 25 in that this surface 725 is planar, the peripheral portion of this lateral surface 4'''A of the running part 4''' of the associated nail 1''', to be covered by the surface 725, also being provided to be planar so as to form, between the surfaces 725 and 4'''A, a planar contact interface oriented perpendicular to the fastening axis Z720. In order for the bar 721 to be blocked in translation relative to the implant 1''' in the plane of the aforementioned interface, the mechanism 722 includes a blocking element 729, here in the form of a pull-tab movable parallel to the axis Z720 to engage in a complementary cavity 4'''.2, defined in a hollow in the surface 4'''A.

Various arrangements and alternatives of the instrumentation I described thus far can also be considered. In particular, the different embodiments may be combined with one another at least in part to create new embodiments. Likewise, the retro-impaction system 30 described above may be integrated into all of the alternatives of the instrumentation I.

Furthermore, the instrumentation I considered thus far may, in an alternative that is not shown, be designed to implant types of elongated implants other than osteosynthesis nails, such as the nails 1, 1', 1" end 1'''. In particular, the instrumentation I may be used to implant a rectilinear prosthetic rod, for example to implant, in the diaphysis of the humerus, a humeral rod of a shorter prosthesis: in this case, the corresponding implantation method is in particular adapted by providing, at the beginning of the surgical method, that the head, or more generally the proximal end, of the long bone in which the prosthetic rod is to be implanted, is either resected, or removed by removing at least one of its fragments when this proximal end is fractured into several fragments and the long bone is fractured between its proximal end and its diaphysis.

The invention claimed is:

1. A surgical instrumentation for implanting a rectilinear elongated implant in a long bone, the implant defining a longitudinal axis and including two opposite terminal parts, each of which is provided with at least one hole suitable to receive a fastening element to fasten the implant to the long bone, and a running part that separates the two terminal parts from one another, the terminal parts and the running part being in rectilinear alignment along the longitudinal axis,
wherein said instrumentation comprises a targeting ancillary tool that is adapted to target the at least one hole of each of the two terminal parts of the implant, if applicable percutaneously, along at least one targeting axis that is transverse to the longitudinal axis, and
wherein the targeting ancillary tool is designed to be fastened laterally directly to the running part of the implant so as to position the targeting ancillary tool and the implant relative to one another in a predetermined configuration.

2. The instrumentation according to claim 1, wherein the targeting ancillary tool is designed to be fastened exclusively laterally to the running part of the implant, without interacting with the terminal parts of the implant.

3. The instrumentation according claim 1, wherein the instrumentation comprises a bar suitable for connecting the targeting ancillary tool and the running part of the implant to one another, extending lengthwise along a fastening axis that is transverse to the longitudinal axis, said bar being provided with a mechanism for lateral connection to the implant, which rigidly connects the bar to the running part of the implant and which guides the relative positioning of the implant and the bar to the predetermined configuration.

4. The instrumentation according to claim 3, wherein the bar is supported removably by the targeting ancillary tool.

5. The instrumentation according to claim 3, wherein the bar is permanently secured to the targeting ancillary tool.

6. The instrumentation according to claim 3, wherein the mechanism includes a rod having a distal part, which is arranged at a distal part of the bar, opposite the targeting ancillary tool , and which is designed to be rigidly connected to the running part of the implant.

7. The instrumentation according to claim 6, wherein the distal part of the rod is threaded so as to be able to be screwed:
either in a complementary tapping of a through hole of the running part of the implant,
or in an expansion pin of the mechanism, to be placed in a complementary transverse hole of the running part of the implant.

8. The instrumentation according to claim 6, wherein the distal part of the rod includes a bearing stop that presses the running part of the implant laterally when a part of the rod, separate from the distal part of the rod, is engaged with the distal end of the bar.

9. The instrumentation according to claim 6, wherein the rod extends along the bar, from the distal part of the rod to the targeting ancillary tool, and includes a proximal part, which emerges from the targeting ancillary tool on the side thereof opposite the bar and that is provided with an actuating element of the rod.

10. The instrumentation according to claim 3, wherein the mechanism includes a guiding surface for guiding positioning of the implant, which is fixedly secured by the bar and is configured to cover a peripheral portion of a lateral surface of the running part of the implant.

11. The instrumentation according to claim 10, wherein the guiding surface has a V- or C-shaped profile for stabilizing the implant.

12. The instrumentation according to claim 10, wherein the guiding surface is planar and wherein the mechanism further includes an element for blocking the translation, in the plane of the guiding surface, of the bar relative to the implant.

13. The instrumentation according to claim 3, wherein the instrumentation further comprises a retro-impaction system suitable for applying impacts that are transmitted from the targeting ancillary tool to the running part of the implant via the bar.

14. A surgical assembly, including:
a rectilinear elongated implant, defining a longitudinal axis and including two opposite terminal parts, each of which is provided with at least one hole suitable to receive a fastening element to fasten the implant to a long bone, and a running part that separates the two terminal parts from one another, the terminal parts and the running part being in rectilinear alignment along the longitudinal axis, and
an instrumentation for implanting the implant in a long bone, said instrumentation being according to claim 1.

15. The assembly according to claim 14, wherein the implant is a humeral osteosynthesis nail.

16. The assembly according to claim 14, wherein the running part extends symmetrically about the longitudinal axis.

17. A surgical method for implanting a rectilinear osteosynthesis nail in a long bone, said long bone being fractured at least between its proximal end and its diaphysis, in which method:
the nail has a longitudinal axis and includes two opposite terminal parts, each of which is provided with at least one hole suitable to receive a fastening element to fasten the nail to the long bone, and a running part that separates the two terminal parts from one another, the terminal parts and the running part being in rectilinear alignment along the longitudinal axis, and a targeting ancillary tool is fastened laterally directly to the running part of the nail, and during which method, successively:

a surgical approach is opened by forming an incision in the soft flesh to access the bone, at the fracture thereof between its proximal end and its diaphysis, after having separated the proximal end from the diaphysis, a first of the two terminal parts of the nail is inserted, via the approach, into the diaphysis, then the targeting ancillary tool is used to place, percutaneously and along a first targeting axis that is transverse to the longitudinal axis of the nail, at least one first fastening element in the at least one hole of the first terminal part of the nail to fasten the diaphysis and the first terminal part of the nail, after having replaced the proximal end in the longitudinal extension of the diaphysis, the targeting ancillary tool is used to place, percutaneously and along a second targeting axis that is transverse to the longitudinal axis of the nail, at least one second fastening element in the at least one hole of the second terminal part of the nail to fasten the proximal end and the second terminal part of the nail, the running part of the nail is unfastened from the targeting ancillary tool to disengage the nail from the targeting ancillary tool, and the approach is closed.

18. The method according to claim 17, wherein the proximal end forms a single-piece fragment, and during which, after having replaced the proximal end in the longitudinal extension of the diaphysis but before having fastened the proximal end to the second terminal part of the nail, the second terminal part of the nail is retro-impacted inside the proximal end by striking the targeting ancillary tool.

19. The method according to claim 17, wherein the proximal end itself is fractured in several fragments, and during which, after having fastened the diaphysis to the first terminal part of the nail, the fragments of the proximal end are united around the second terminal part of the nail.

20. The method according to claim 19, wherein, after having united the fragments of the proximal end, at least some of the fragments are sutured together, via the approach.

21. The method according to claim 19, wherein after having united the fragments of the proximal end, the targeting ancillary tool is used to place the at least one second fastening element between the second terminal part of the nail and one of the fragments.

22. The method according to claim 17, wherein the approach is deltopectoral.

23. The method according to claim 17, wherein the approach is superolateral.

24. A surgical instrumentation for implanting a rectilinear elongated implant in a long bone, the implant defining a longitudinal axis and including two opposite terminal parts, each of which is provided with at least one hole suitable to receive a fastening element to fasten the implant to the long bone, and a running part that separates the two terminal parts from one another, the terminal parts and the running part being in rectilinear alignment along the longitudinal axis, wherein said instrumentation comprises a targeting ancillary tool that is adapted to target the at least one hole of each of the two terminal parts of the implant, if applicable percutaneously, along at least one targeting axis that is transverse to the longitudinal axis, wherein the targeting ancillary tool is designed to be fastened laterally to the running part of the implant, forming a lateral connection with the implant so as to position the targeting ancillary tool and the implant relative to one another in a predetermined configuration, and wherein the lateral connection is configured to be spaced away from the at least one hole of each of the terminal parts of the implant along the longitudinal axis.

25. The instrumentation according to claim 24, wherein the targeting ancillary tool is designed to be fastened exclusively laterally to the running part of the implant, without interacting with the terminal parts of the implant.

26. A surgical assembly, including:

a rectilinear elongated implant, defining a longitudinal axis and including two opposite terminal parts, each of which is provided with at least one hole suitable to receive a fastening element to fasten the implant to a long bone, and a running part that separates the two terminal parts from one another, the terminal parts and the running part being in rectilinear alignment along the longitudinal axis, and an instrumentation for implanting the implant in a long bone, said instrumentation being according to claim 24.

27. The assembly according to claim 26, wherein the running part extends symmetrically about the longitudinal axis.

28. A surgical method for implanting a rectilinear osteosynthesis nail in a long bone, said long bone being fractured at least between its proximal end and its diaphysis, in which method:

the nail has a longitudinal axis and includes two opposite terminal parts, each of which is provided with at least one hole suitable to receive a fastening element to fasten the nail to the long bone, and a running part that separates the two terminal parts from one another, the terminal parts and the running part being in rectilinear alignment along the longitudinal axis, and a targeting ancillary tool is fastened laterally to the running part of the nail, forming a lateral connection with the nail, the lateral connection being spaced away from the at least one hole of each of the terminal parts of the nail along the longitudinal axis, and during which method, successively:

a surgical approach is opened by forming an incision in the soft flesh to access the bone, at the fracture thereof between its proximal end and its diaphysis, after having separated the proximal end from the diaphysis, a first of the two terminal parts of the nail is inserted, via the approach, into the diaphysis, then the targeting ancillary tool is used to place, percutaneously and along a first targeting axis that is transverse to the longitudinal axis of the nail, at least one first fastening element in the at least one hole of the first terminal part of the nail to fasten the diaphysis and the first terminal part of the nail, after having replaced the proximal end in the longitudinal extension of the diaphysis, the targeting ancillary tool is used to place, percutaneously and along a second targeting axis that is transverse to the longitudinal axis of the nail, at least one second fastening element in the at least one hole of the second terminal part of the nail to fasten the proximal end and the second terminal part of the nail, the lateral connection is disconnected to disengage the nail from the targeting ancillary tool, and the approach is closed.

* * * * *

UNITED STATES PATENT AND TRADEMARK OFFICE
CERTIFICATE OF CORRECTION

PATENT NO. : 10,485,601 B2  
APPLICATION NO. : 15/369178  
DATED : November 26, 2019  
INVENTOR(S) : Benjamin Dassonville et al.

Page 1 of 1

It is certified that error appears in the above-identified patent and that said Letters Patent is hereby corrected as shown below:

On the Title Page

Item (72), Inventors, Line 5, delete "Lyons" and insert --Lyon--.

In the Claims

In Column 13, Line 55, Claim 3, delete "according" and insert --according to--.

In Column 14, Line 4, Claim 6, delete "tool ," and insert --tool,--.

Signed and Sealed this  
Ninth Day of March, 2021

Drew Hirshfeld  
*Performing the Functions and Duties of the*  
*Under Secretary of Commerce for Intellectual Property and*  
*Director of the United States Patent and Trademark Office*